US 11,407,661 B2

(12) United States Patent
McCague et al.

(10) Patent No.: US 11,407,661 B2
(45) Date of Patent: Aug. 9, 2022

(54) CHLORINE GENERATOR SYSTEM

(71) Applicant: Watkins Manufacturing Corporation, Vista, CA (US)

(72) Inventors: Michael McCague, Escondido, CA (US); Paul Oddou, Oceanside, CA (US)

(73) Assignee: Watkins Manufacturing Corporation, Vista, CA (US)

(*) Notice: Subject to any disclaimer, the term of this patent is extended or adjusted under 35 U.S.C. 154(b) by 198 days.

(21) Appl. No.: 15/651,709

(22) Filed: Jul. 17, 2017

(65) Prior Publication Data
US 2019/0016614 A1  Jan. 17, 2019

(51) Int. Cl.
C02F 1/467 (2006.01)
C02F 1/461 (2006.01)
C02F 103/42 (2006.01)
A61L 2/26 (2006.01)
A61L 2/18 (2006.01)

(52) U.S. Cl.
CPC .............. *C02F 1/4674* (2013.01); *A61L 2/18* (2013.01); *A61L 2/26* (2013.01); *C02F 1/46109* (2013.01); *C02F 2103/42* (2013.01); *C02F 2201/006* (2013.01); *C02F 2201/4614* (2013.01)

(58) Field of Classification Search
CPC .............. C02F 1/4674; C02F 1/46109; C02F 2201/4614; C02F 2201/42; A61L 2/26; A61L 2/18
See application file for complete search history.

(56) References Cited

U.S. PATENT DOCUMENTS

| 4,036,726 | A | * | 7/1977 | Gale ....................... C02F 1/463 |
| | | | | 204/229.6 |
| 4,290,873 | A | * | 9/1981 | Weaver ............... C02F 1/46109 |
| | | | | 204/230.2 |
| 4,525,253 | A | * | 6/1985 | Hayes ................... C02F 1/4606 |
| | | | | 204/229.2 |
| 4,781,805 | A | | 11/1988 | Dahlgren |
| 5,324,398 | A | | 6/1994 | Erickson et al. |
| 5,328,584 | A | | 7/1994 | Erickson et al. |
| 6,821,398 | B2 | | 11/2004 | Von Broembsen |
| 7,455,754 | B2 | | 11/2008 | Wesner et al. |
| 8,163,141 | B2 | * | 4/2012 | Von Broembsen ... C02F 1/4674 |
| | | | | 204/269 |
| 8,266,736 | B2 | | 9/2012 | McCague |
| 8,273,254 | B2 | | 9/2012 | McCague |

(Continued)

FOREIGN PATENT DOCUMENTS

EP         1 647 525 A1    4/2006

OTHER PUBLICATIONS

International Search Report, PCT/US 1834957, dated Oct. 22, 2018, 5 pages.

(Continued)

*Primary Examiner* — Louis J Rufo
(74) *Attorney, Agent, or Firm* — Lapple Ubell IP Law, LLP; Franklin D. Ubell

(57) ABSTRACT

A chlorine generator apparatus wherein a housing is adapted to be mounted in an exterior, user-accessible surface of a spa and a chlorine generating electrode cartridge carrying a pair of electrodes is configured to be installable by a user in the housing and to thereafter be removeable by the user for replacement.

56 Claims, 11 Drawing Sheets

(56) References Cited

U.S. PATENT DOCUMENTS

| | | |
|---|---|---|
| 9,493,369 B2 | 11/2016 | McCague |
| 9,878,926 B2 | 1/2018 | Heng et al. |
| 2005/0029116 A1 | 2/2005 | Bulan et al. |
| 2005/0029118 A1* | 2/2005 | Holstein ............... C02F 1/4674 205/618 |
| 2006/0076282 A1 | 4/2006 | Hui et al. |
| 2006/0091002 A1 | 5/2006 | Hin et al. |
| 2006/0249400 A1 | 11/2006 | Bremauer |
| 2007/0084770 A1 | 4/2007 | Mikuski et al. |
| 2009/0173638 A1* | 7/2009 | Powell ................... C02F 1/463 205/688 |
| 2010/0101010 A1* | 4/2010 | McCague ............. C02F 1/4674 4/496 |
| 2011/0010835 A1* | 1/2011 | McCague ............. C02F 1/4674 4/494 |
| 2012/0012209 A1* | 1/2012 | Andrews ............... C02F 1/4674 137/599.15 |
| 2012/0012466 A1 | 1/2012 | Sperry et al. |
| 2013/0105372 A1 | 5/2013 | Chen et al. |
| 2014/0367344 A1* | 12/2014 | Faure ................... C02F 1/4606 210/748.18 |
| 2015/0203376 A1 | 7/2015 | Heng et al. |
| 2017/0152162 A1* | 6/2017 | Cam ................... C02F 1/46109 |

OTHER PUBLICATIONS

Written Opinion of the International Searching Authority, dated Oct. 22, 2018, 8 pages.
EPO 18836168.7 Extended European Search Report and Search Opinion, dated Jul. 17, 2020.

* cited by examiner

CHLORINE GENERATOR SYSTEM

FIELD

The subject disclosure relates to chlorine generating systems and more particularly to a chlorine generator system for spas, tubs, pools and the like which features a disposable and consumer replaceable electrode cartridge.

DESCRIPTION OF RELATED ART

Various chlorine generating devices have been constructed in the past, for example, such as the drop-in chlorinator disclosed in U.S. Pat. No. 8,745,774, assigned to Watkins Manufacturing Corporation of Vista, Calif.

SUMMARY

Illustrative embodiments provide a chlorine generator installed in a spa and having a disposable and consumer replaceable electrode cartridge.

According to one embodiment, a chlorine generator apparatus comprises a housing adapted to be mounted in a user-accessible exterior surface of a spa and a chlorine generating electrode cartridge mounted in the housing and carrying first and second electrodes wherein the electrode cartridge is configured to be replaceable by a user.

According to another aspect of the disclosure, a housing is provided for receiving an electrode cartridge comprising a wall fitting mounted to a consumer-accessible surface of a spa and a cap removably attachable to the wall fitting by a user to provide user access to the electrode cartridge. In one embodiment, the housing may further comprise a lower housing section attached to a lower end of the wall fitting. The lower housing section may provide an electrode chamber wherein electrodes of the electrode cartridge may be disposed to generate chlorine for sanitizing the spa water According to another aspect, an electrode cartridge adapted to be installed into a housing by a user of a spa is provided comprising a handle component grippable by the user to insert the electrode cartridge into the housing and to pull the electrode cartridge out of the housing for replacement. In one embodiment, first and second electrodes are mounted beneath the handle for generating chlorine from spa water, and first and second electrical contacts are positioned to come into electrical contact with first and second electrical contacts located on an interior surface of the housing when the electrode cartridge is in an installed position in the housing.

According to another aspect, an electrode cartridge is provided comprising first and second electrodes each of which include a vertical portion which forms into a horizontal base portion from which extends an outwardly curved spring arm electrical contact. According to another aspect, the horizontal base portions of each of the first and second electrodes respectively fit into a respective mating opening in an electrode cup. In one embodiment, each horizontal base portion may be held in place by a bottom surface of a handle component of the electrode cartridge.

According to another aspect, a chlorine generator apparatus is provided wherein a housing comprises first and second internal electrical contact terminals formed on an inner surface thereof and wherein spring arm portions of the first and second electrodes of an electrode cartridge form electrical contact surfaces which are positioned to make electrical contact with the first and second internal electrical contact terminals when the electrode cartridge is fully inserted into the housing.

According to another aspect, a chlorine generator apparatus is provided comprising a groove formed in an inner wall of an electrode cartridge housing and first and second locking bars having first and second projections on respective outer ends thereof and mounted to slide laterally in an electrode cartridge such that the first and second projections can come into engagement with the groove in the housing inner wall in order to lock the electrode cartridge in position. A spring loaded plunger mounted in the electrode cartridge is shaped and positioned to cause the first and second locking bars to move laterally such that the first and second projections come into engagement with the groove.

DETAILED DESCRIPTION

Figure 1:
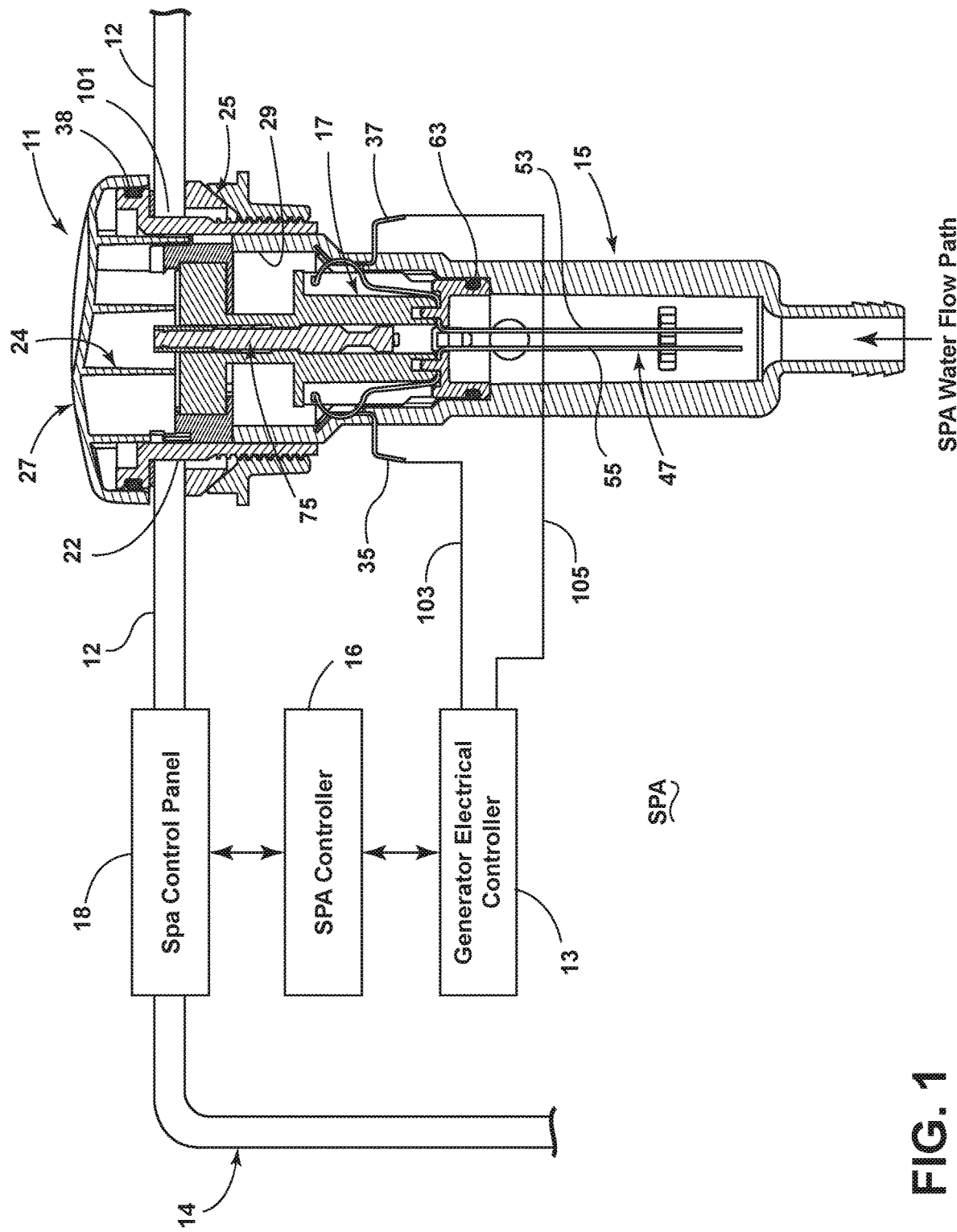
FIG. 1 is a schematic side view of a chlorine generator system according to an illustrative embodiment installed in a spa.
Figure 3:
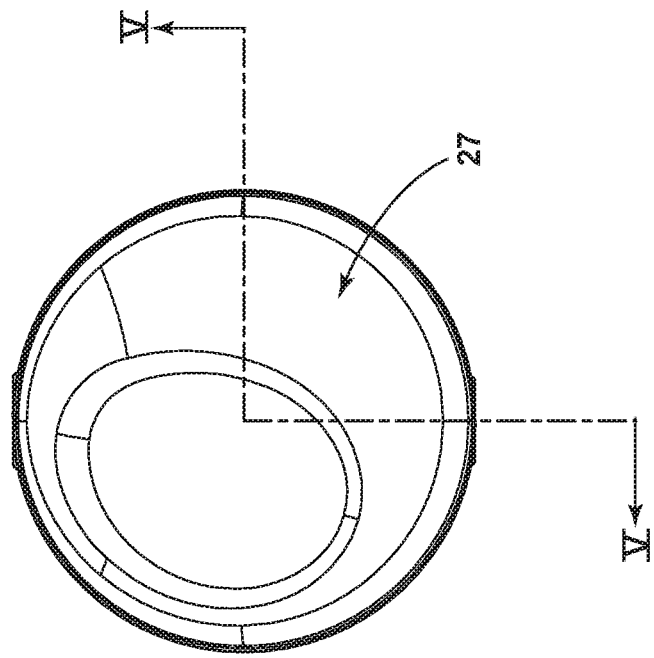
FIG. 3 is a top view of the chlorine generator of FIG. 2.
Figure 2:
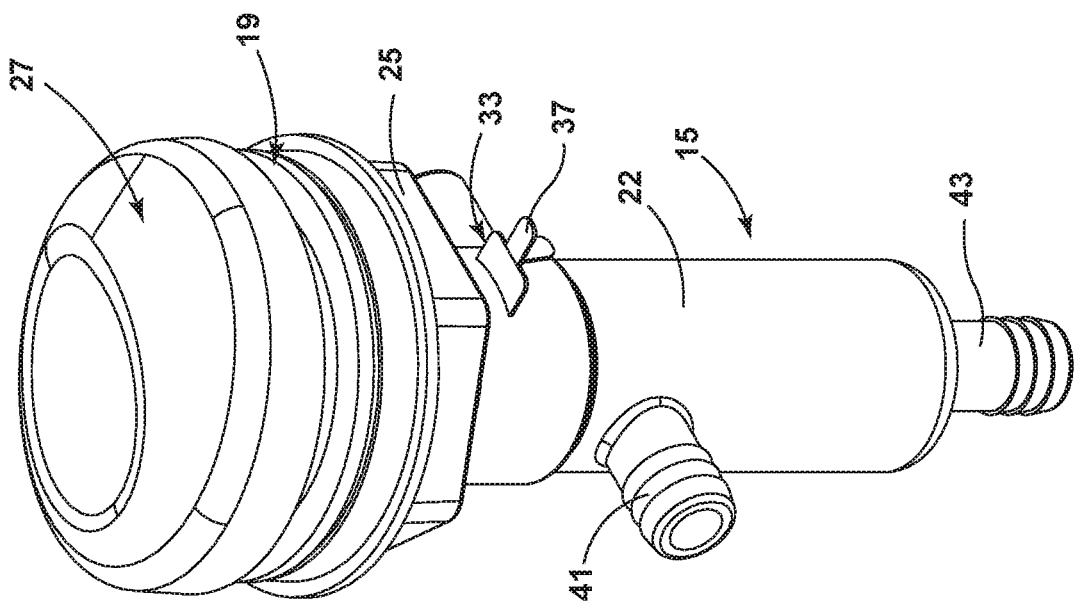
FIG. 2 is a perspective view of the chlorine generator employed in the system of FIG. 1.
Figure 4:
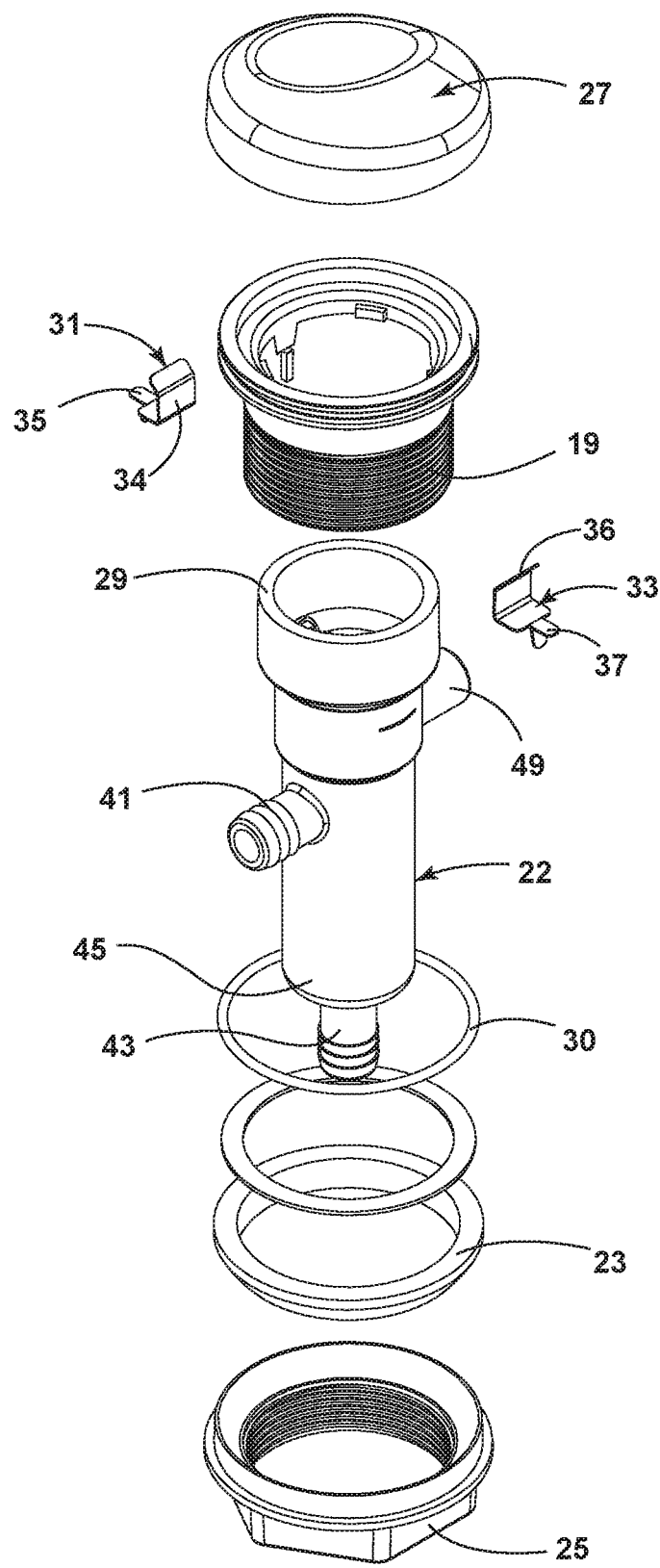
FIG. 4 is an exploded perspective view of the electrode housing of the chlorine generator of FIG. 2.
Figure 5:
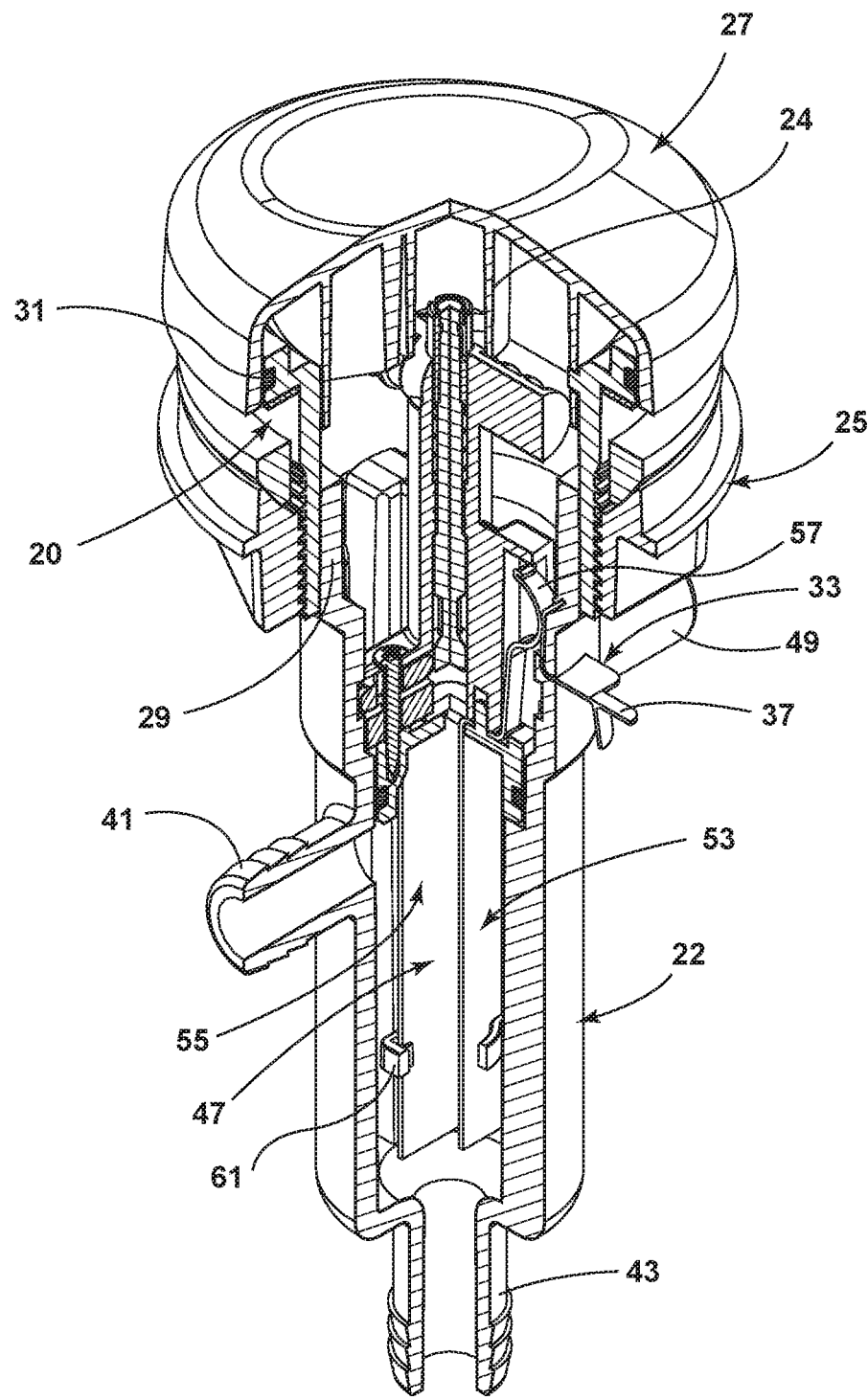
FIG. 5 is a sectional perspective view of the chlorine generator of FIG. 2 taken at V-V of FIG. 3.
Figure 7:
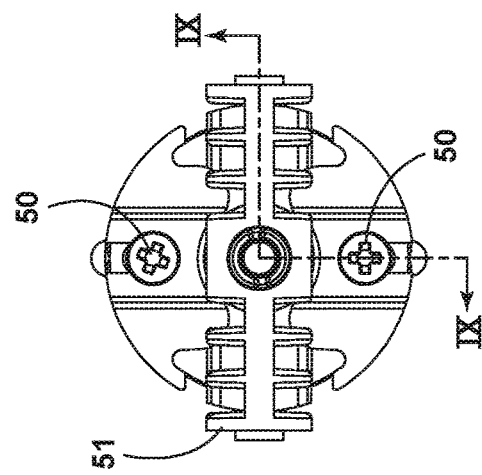
FIG. 7 is a top view of the electrode cartridge component of FIG. 6.
Figure 6:
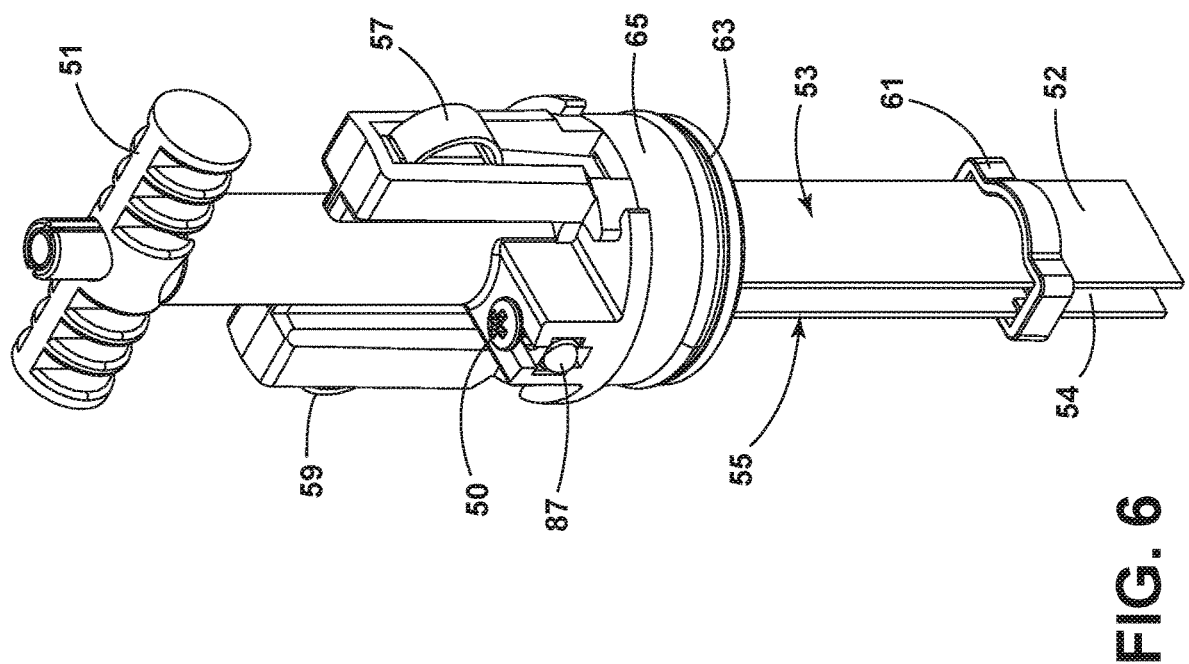
FIG. 6 is a perspective view of an electrode cartridge component of the chlorine generator of FIG. 2.

A chlorine generator system according to an illustrative embodiment is shown in FIG. 1. The illustrative system includes an electrical controller 13 and a chlorine generator 11 mounted in a bar top 12 of a spa 14. As may be appreciated, the bar top is an example of a user accessible surface of the spa where a user may be, for example, a user or owner of the spa 14. In one embodiment, the spa 14 may be a portable spa.

The chlorine generator 11 comprises an electrode cartridge housing 15 and an electrode cartridge 17. In the illustrative embodiment, the electrode cartridge 17 carries a pair of electrodes 53, 55, and is removably installed in the electrode cartridge housing 15. In one embodiment, the housing 15 is keyed to the electrode cartridge 17 to insure that the cartridge 17 may only be installed in the housing 15 in a proper manner. In an illustrative embodiment, water from the spa circulation path is routed up to the housing 15, through the electrodes 53, 55 and back out of the housing 15 to the spa 14.

In an illustrative embodiment, the electrical controller 13 controls generation of chlorine by the electrode cartridge 17. In one embodiment, the electrical controller 13 is relatively small in size, powered through the spa control system 16, and fully integrated into the spa 14. In one embodiment, the electrical controller 13 utilizes an RS485 communication protocol to transmit data and communicate with the spa control system 16. In one embodiment, the spa control system 16 may be accessed through and driven by a spa control panel 18. In another embodiment, a closed loop control system may be employed which includes a sensor which measures, for example, one or more of: chlorine, bromine, ozone, ORP, pH, conductivity, alkalinity, cyanuric acid, water hardness and/or temperature. The sensor then feeds parameters to an electronic controller which then automatically causes generation of the appropriate amount of chlorine via the chlorine generator 11.

In the illustrative embodiment, operation of the chlorine generator 11 is controlled by user settings for chlorine output made at the spa control panel 18. In an illustrative embodiment, the electrical controller 13 drives the electrodes of the chlorine generator 11 in a constant current mode to enable an optimal or desired chlorine generation rate. This mode of operation also allows the system to be driven at different specific current levels to control the generation rate of chlorine per hour depending on the user settings.

In one embodiment, the spa water is salted, for example, by adding sodium chloride to achieve a concentration of, for example, 2000 ppm. Such an embodiment may be characterized as a salt water chlorinator system.

As shown in FIGS. 2-5, in an illustrative embodiment, the electrode cartridge housing 15 comprises a wall fitting 19, which has circular groove 20, which receives an edge, e.g. 101 (FIG. 1), of the spa bar top 12. The wall fitting 19 mounts to the bar top 12 via a centering ring 23 and a nut 25. A cap 27 is screwed to the wall fitting 19 on the user side of the system to provide access to the electrode cartridge 17. An internal web portion 24 of the cap 27 also positions and holds the electrode cartridge 17 in place during operation.

In an illustrative embodiment, an upper portion 29 of a lower housing section 22 glues into or otherwise attaches to the wall fitting 19 to form a watertight attachment. An O-ring 30 mounts in a receptacle in the wall fitting 19 and provides a watertight seal between the wall fitting 19 and the cap 27. In illustrative embodiments, the wall fitting 19, cap 27, and lower housing section 22, may all be a suitable molded plastic material, such as, for example PVC or ABS plastic.

In the illustrative embodiment, the electrical connection of the electrode cartridge 17 to the controller 13 via electrical leads 103, 105 (FIG. 1) is completed through a pair of titanium electrical contacts 31, 33, which are molded into the housing 15 in watertight fashion. The contacts 31, 33 have flat vertical terminals 34, 36 adjacent an inside surface of the housing 15, as well as quick disconnect terminals 35, 37 on the outside of the housing 15. The electrical contacts 31, 33 thus enable dry electrical connections to the chlorine generator 11 and ease of service of the system.

Below the electrical contacts 31, 33 is a drain port 41. This port 41 allows for removal of any water that may have entered the dry portion of the housing 15 during removal and replacement of the electrode cartridge 17. A water inlet port 43 on the bottom 45 of the housing 15 allows spa water to enter the housing 15 and flow through the wet electrode chamber 47. At the top of the wet electrode chamber 47 is an outlet port 49 through which the chlorinated spa water flows into the spa 14. The vertical water flow through the housing 15 ensures efficient flushing of the housing 15 and removal of all liquids and gases generated in the housing 15 during operation of the chlorinator 11.

As shown in FIGS. 6-9, in an illustrative embodiment, the electrode cartridge 17 comprises a tee handle 51 and pair of mixed metal oxide titanium electrodes 53, 55. In illustrative embodiments, the electrodes 53, 55 may comprise, for example, titanium or niobium base metal with a suitable oxide coating, such as, for example, ruthenium oxide, iridium oxide, or platinum oxide. In other embodiments, the electrodes could be boron/nitrogen doped diamond.

In the illustrative embodiment, the electrodes 53, 55 are each formed as a single piece and each includes a respective rectangular vertical portion 52, 54, which forms into a respective horizontal base portion 56, 58, from which extends a respective outwardly curved spring arm electrical contact 57, 59. The electrodes 53, 55 could of course be formed of multiple parts in other embodiments, for example, with separate wet electrode and spring contact components.

The horizontal base portions 56, 58 of each of the electrodes 53, 55 each fit into a respective mating opening 67, 69 in an electrode cup 65 and are held in place by a bottom surface 71 of the tee handle 51. An O-ring 63 provides a watertight seal between the housing 15 and the electrode cup 65.

First and second slots, e. g. 99, are defined in the electrode cup 65 on either side of horizontal projections 110, 111, through which a respective one of the electrodes 53, 54 are inserted. Potting material is applied to seal openings around the electrodes 53, 54. A cap 181 covers the opening in the electrode cup 65 and prevents potting material from leaking up through the opening. In an illustrative embodiment, the tee handle 51 and electrode cup 65 may be molded plastic components formed, for example, of PVC or ABS plastic.

In an illustrative embodiment, the design and shape of the electrodes 53, 55 provide a single piece component extending from the wetted electrode blade portions 52, 54 to the dry spring arm electrical contacts 57, 59. The wetted blade portions 52, 54 of the electrodes 53, 55 are equally spaced apart down the length of the cartridge 17, and a spacer 61 is mounted at the end of the cartridge 17 to ensure that the electrodes 53, 55 are held in proper position. The dry spring arm portions 57, 59 of the electrodes 53, 55 form electrical contact surfaces which are spring-biased into electrical contact with the flat vertical electrical contact terminals 34, 36, located on the interior of the electrode housing 15.

Figure 13:
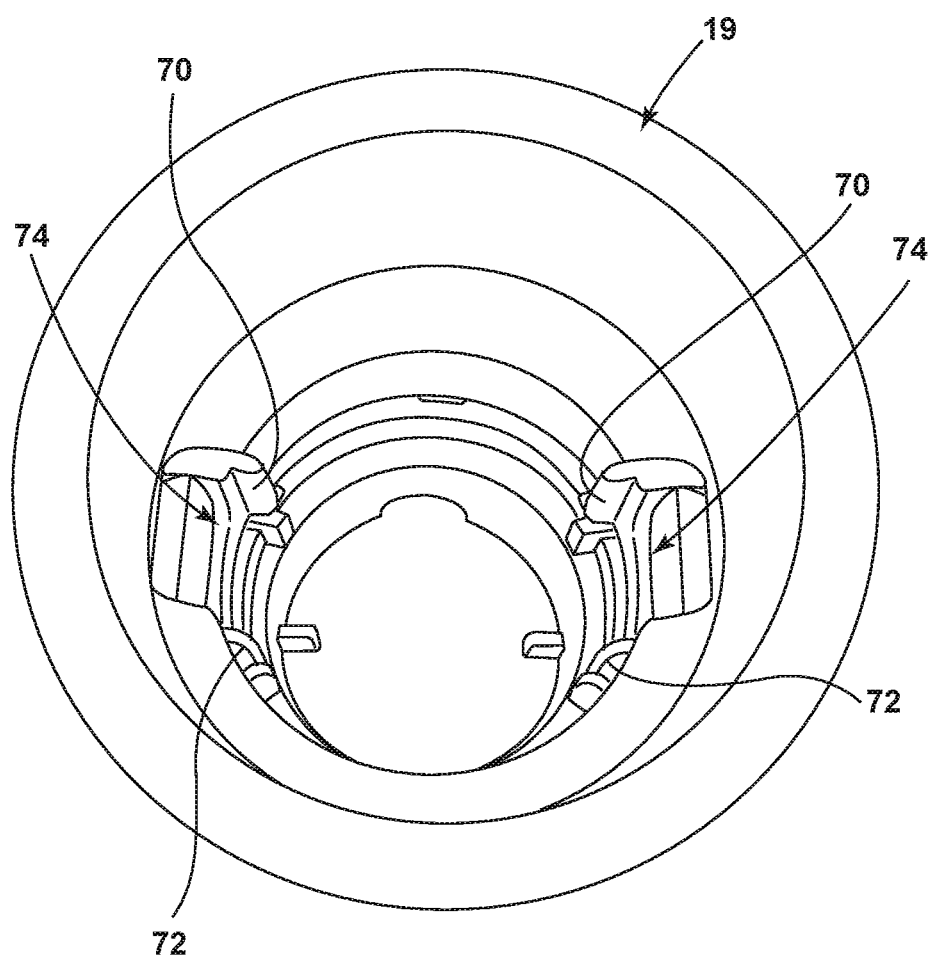
FIG. 13 is a perspective view of the open upper end of the electrode housing of FIG. 4.

As noted above, in one embodiment, the geometry of the electrode cartridge 17 permits installation of the electrode cartridge 17 into the housing 15 in only one direction and orientation, insuring proper electrical contact. In particular, in the illustrative embodiment, the outer vertical edges of the rectangular plastic guards, 60, 62 around each of the electrode contact arms 57, 59 extend outwardly and are shaped to mate with respective channels 74 defined by vertical guides 70, 72 formed on the inner wall of the electrode housing 19, as shown in FIG. 13. The electrode cartridge 17 is thereby keyed to the housing 19, permitting the cartridge 17 to be inserted in only one orientation.

Figure 8:
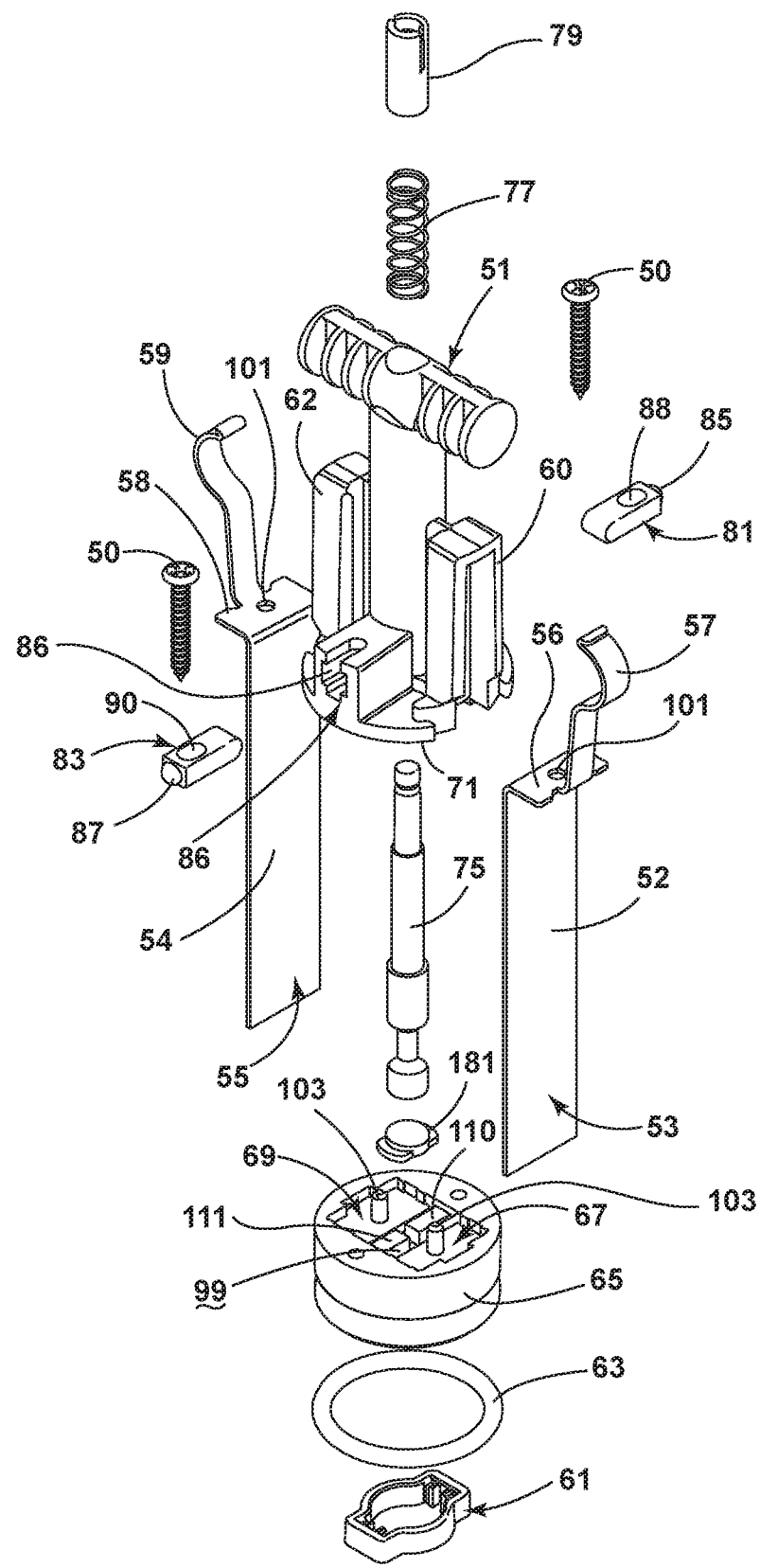
FIG. 8 is an exploded perspective view of the electrode cartridge component of FIG. 6.
Figure 9:
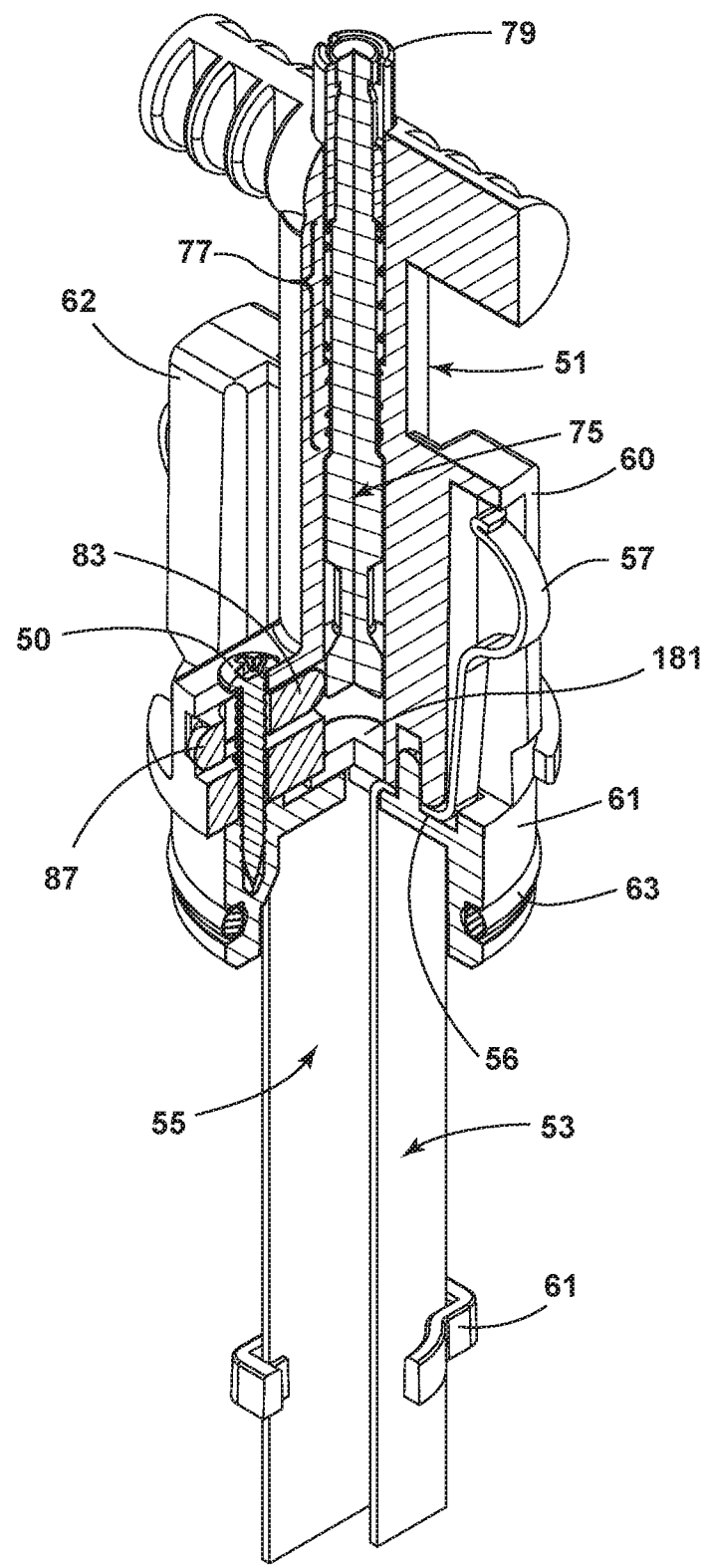
FIG. 9 is a perspective sectional view of the electrode cartridge component of FIG. 6 taken at IX-IX of FIG. 7.

In one illustrative embodiment, a locking mechanism is used to secure the cartridge 17 in place within the housing 15 independent of the cap 27. In particular, as shown in FIGS. 8 and 9, a spring loaded plunger is slidably mounted in an internal opening in the tee handle 51 and comprises a bottom shaft 75, a spring 77 and a plunger cap 79. Respective locking bars 81, 83 with ball-shaped end surfaces 85, 87 are positioned to move laterally in respective channels 86, 88 (FIG. 10) formed in the lower end of the tee handle 51. Oblong slots 88, 90, are formed in each of the locking bars 81, 83 to permit the locking bars 81, 83 to move laterally left and right with respect to the attachment screws 50, which attach the tee handle 51 to the electrode cup 65.

Figure 10:
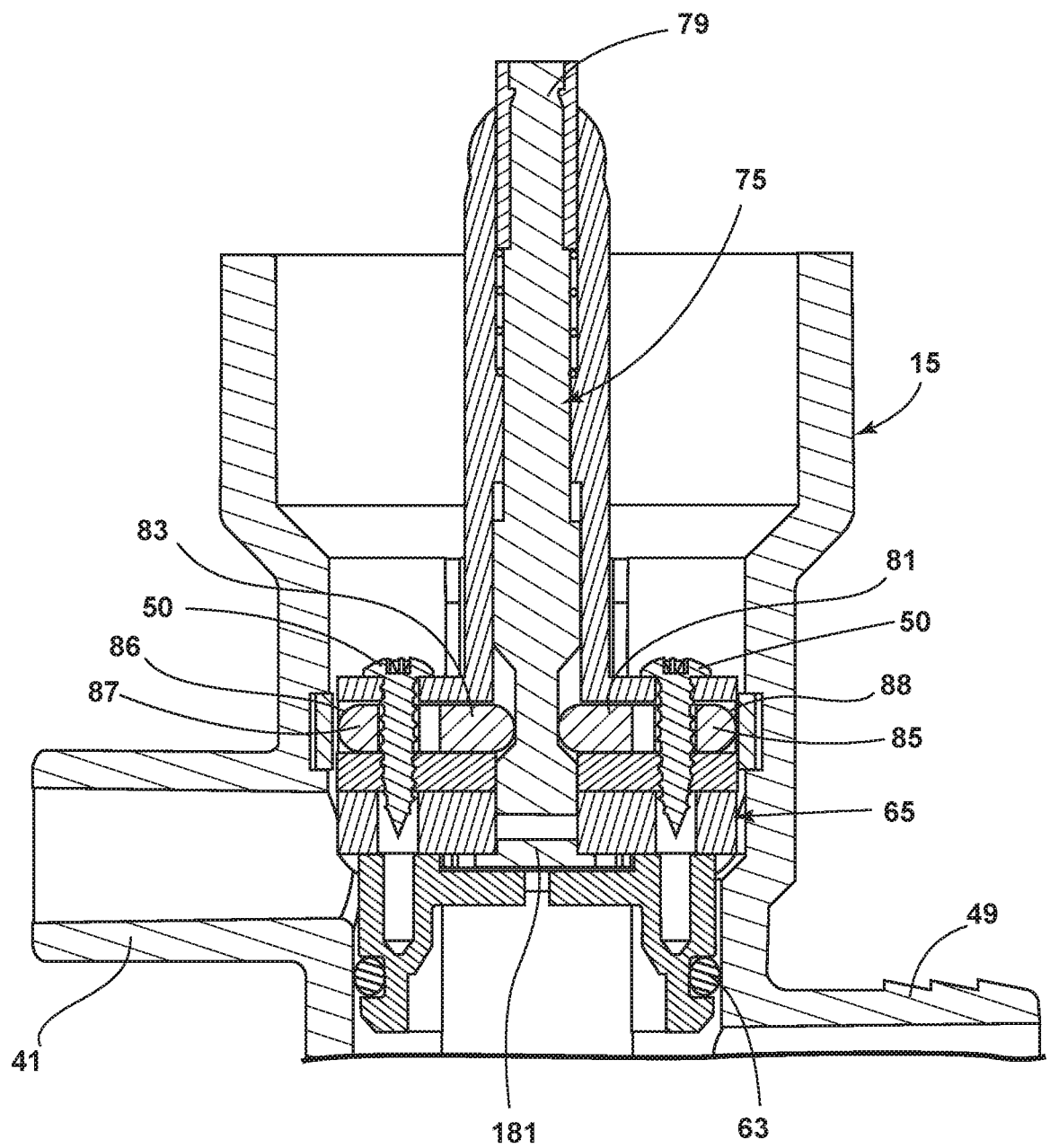
FIG. 10 is a sectional view illustrative of an electrode cartridge locking mechanism according to an illustrative embodiment in a first position.
Figure 11:
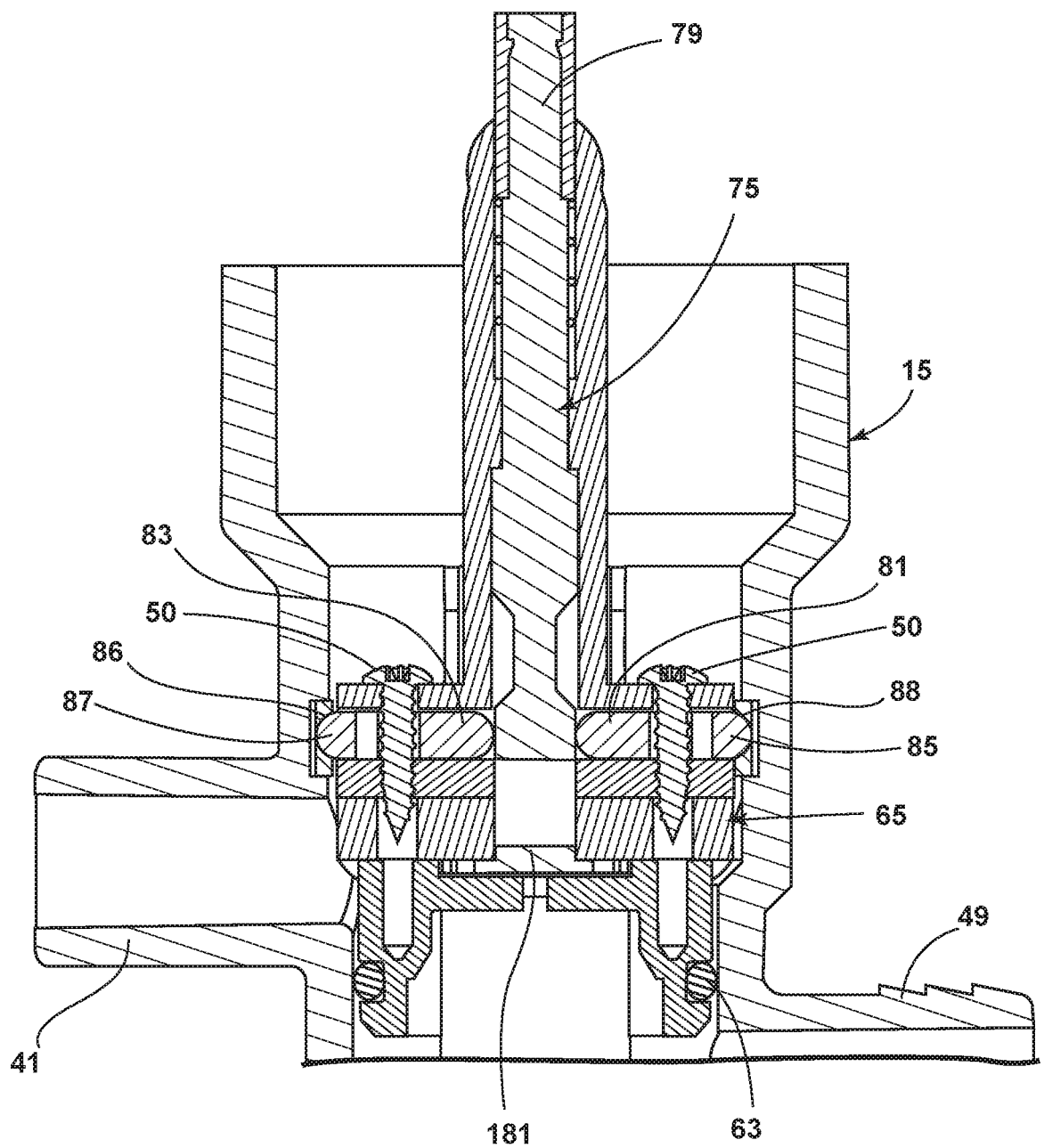
FIG. 11 is a sectional view of the illustrative electrode cartridge locking mechanism of FIG. 10 in a second position.
Figure 12:
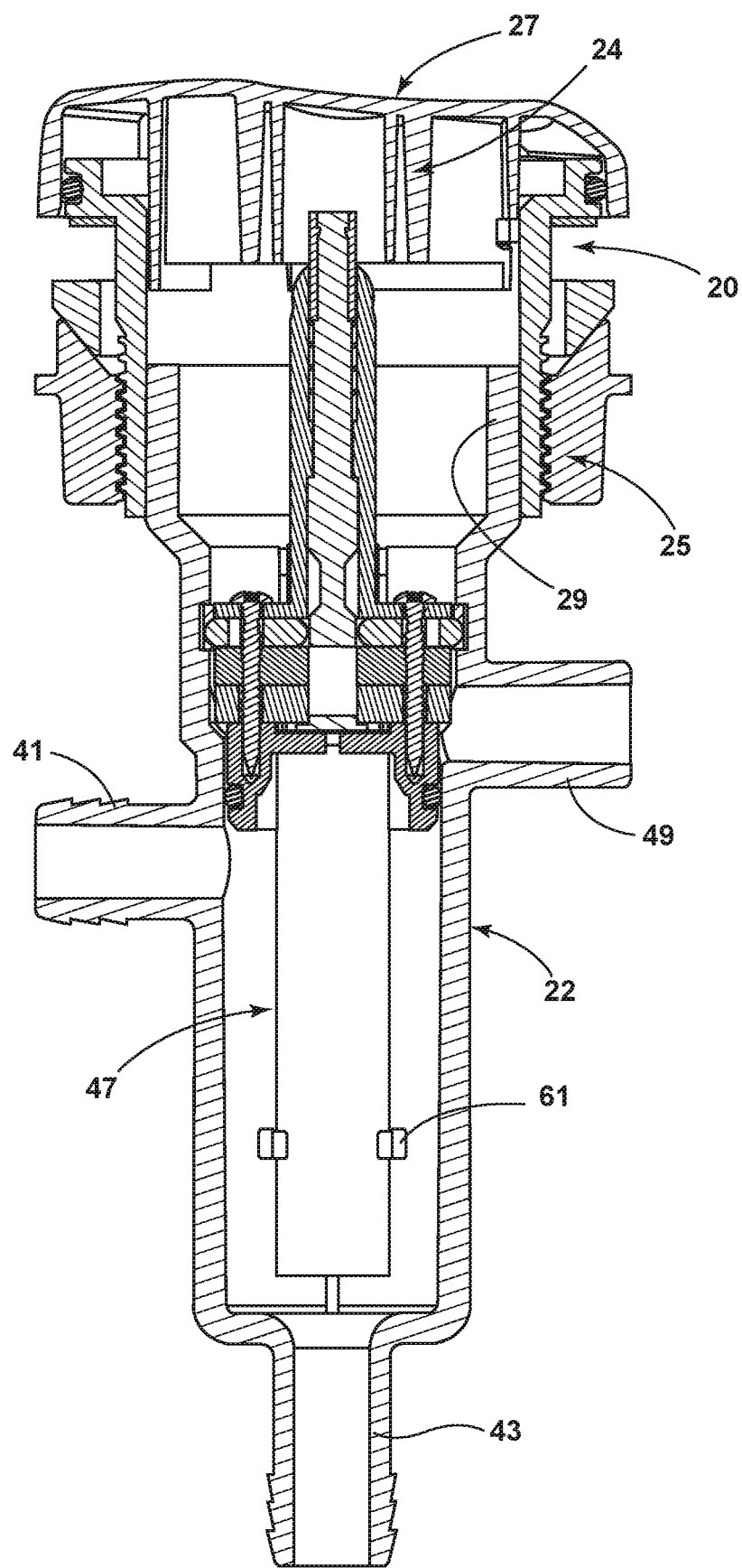
FIG. 12 is a sectional view of the chlorine generator of FIG. 2.

As a result of this construction, the cartridge 17 cannot be installed in the housing 15 without first pushing the plunger down by depressing the plunger cap 79 to retract the balls 85, 87 to a position within the respective channels 86, 88 in the lower end of the handle 51, as illustrated in FIG. 10. Once the balls 85, 87, are positioned adjacent the channel 90 in the housing 15, as shown in FIG. 10, the plunger can be pulled upward to the position shown in FIG. 11 so as to force lateral movement of the locking bars 81, 83, thereby causing the balls 85, 87 to enter the locking position shown in FIG. 11. If the cartridge 17 is not fully inserted into its proper position in the housing 15, the dimensioning of the cap 27 will cause the cap 27 to push the cartridge 17 into the locked position of FIG. 11 when the cap 27 is installed. If the cap 27 is thereafter removed, the cartridge 17 remains in its proper place.

To remove the cartridge 17, the tee handle 51 may be grasped with two fingers and the plunger cap 79 depressed with the thumb, thereby releasing the locking balls 85, 87 and allowing them to slide back. The cartridge 17 may then be lifted out of the housing 19.

Illustrative embodiments provide numerous advantages and improvements and in particular a low cost, disposable, consumer replaceable electrode cartridge, which is removable from the top side of a spa. Illustrative embodiments enable dry removal of the electrode cartridge, avoiding the risk of electrical shock. Spa-side control and operation of the system is also provided.

Significantly lower water maintenance requirements are also achieved by illustrative embodiments because the electrode cartridge is designed to last a short life and to be disposable. Hence, the necessity to control spa water parameters in order to maintain chlorine generator electrodes in operating condition is minimized or eliminated. For example, softening the spa water can help to minimize the need to clean the electrodes. The illustrative embodiments eliminate the need to clean the electrodes and hence the need to control spa water parameters in order to maintain the electrodes. Thus, when the electrode cartridge is spent (no longer operating in spec) the system instructs the owner to change it out.

From the foregoing, those skilled in the art will appreciate that various adaptations and modifications of the just described illustrative embodiments can be configured without departing from the scope and spirit of the invention. Therefore, it is to be understood that, within the scope of the appended claims, the invention may be practiced other than as specifically described herein.

What is claimed is:

1. An electrode cartridge constructed to generate chlorine and to purify spa water and shaped to be installed into and removed from a housing by a user of a spa, the electrode cartridge comprising:
 a handle grippable by the user to insert the electrode cartridge into the housing and to pull the electrode cartridge out of the housing for replacement;
 an electrode holder located beneath the handle;
 first and second electrodes mounted in said electrode holder and positioned to extend downwardly from a bottom surface of the electrode holder so as to extend into said housing when the electrode cartridge is in an installed position in the housing, the first and second electrodes being selected to generate chlorine to purify spa water, the first and second electrodes being spaced horizontally apart so as to create a flow path for electrical current between them; and
 first and second electrical contacts so positioned on the electrode cartridge as to respectively contact first and second electrical contacts on the housing into which the electrode cartridge is shaped to be installed when the electrode cartridge is in an installed position in the housing.

2. The electrode cartridge of claim 1 further comprising a first electrical conductor path electrically connecting said first electrode with the first electrical contact of the electrode cartridge and a second electrical conductor path electrically connecting said second electrode with the second electrical contact of the electrode cartridge.

3. The electrode cartridge of claim 1 wherein the first and second electrodes each include a vertical portion which forms into a horizontal base portion from which extends an outwardly curved spring arm electrical contact, each outwardly extending spring arm electrical contact comprising one of said first and second electrical contacts positioned on said electrode cartridge.

4. The electrode cartridge of claim 3 wherein the electrode holder is shaped to be insertable into said housing and wherein the electrode holder further comprises first and second horizontally lying receptacles shaped such that the horizontal base portions of each of the first and second electrodes respectively fit therein.

5. The electrode cartridge of claim 4 wherein a bottom surface of the handle of the electrode cartridge is configured to hold each horizontal base portion in place in its respective receptacle.

6. The electrode cartridge of claim 1 wherein the electrical contacts of the electrode cartridge are so further positioned that upon initial installation of the electrode cartridge into the housing, they are initially located above and spaced vertically apart from the first and second contacts located on the housing and thereafter come into electrical contact with a respective one of the first and second contacts located on the housing as the electrode cartridge is inserted further into the housing.

7. The electrode cartridge of claim 1 wherein the electrode cartridge is designed and constructed to be removed as a unit from the housing and thrown away.

8. The electrode cartridge of claim 1 wherein the electrode cartridge is configured such that the first and second electrical contacts of the electrode cartridge constitute the only respective entry and exit points for electrical current into and out of the electrode cartridge.

9. The electrode cartridge of claim 1 so constructed that the flow path of electrical current through the electrode cartridge is broken by the single step of pulling the electrode cartridge out of the housing.

10. The electrode cartridge of claim 1 wherein the electrode cartridge comprises a free standing unit wherein, as a free standing unit, said first and second electrical contacts of the electrode cartridge constitute the only respective entry and exit points for electrical current into and out of the cartridge.

11. The electrode cartridge of claim 1 wherein no electrical wires enter the electrode cartridge.

12. The electrode cartridge of claim 1 wherein no electrical wires are attached to the electrode cartridge.

13. An electrode cartridge comprising:
a single piece first electrode including a vertical portion configured to generate chlorine, the vertical portion forming into a horizontal base portion from which extends an outwardly curved spring arm electrical contact; and
a single piece second electrode including a vertical portion configured to generate chlorine, the vertical portion forming into a horizontal base portion from which extends an outwardly curved spring arm electrical contact.

14. The electrode cartridge of claim 13 wherein each outwardly curved spring arm electrical contact extends upwardly from its respective horizontal base portion.

15. An electrode cartridge configured to generate chlorine and adapted to be installed into a housing by a user of a spa and comprising:
a handle grippable by the user to insert the electrode cartridge into the housing and to pull the electrode cartridge out of the housing for replacement; first and second electrodes mounted beneath the handle for generating chlorine from spa water; and
first and second electrical contacts positioned to respectively contact first and second electrical contacts on the housing into which the electrode cartridge is adapted to be installed when the electrode cartridge is in an installed position in the housing; the electrode cartridge further comprising:
first and second locking bars having first and second projections on respective outer ends thereof and mounted to slide laterally in said cartridge such that said first and second projections can come into engagement with a groove on the housing to lock said cartridge in position; and
a spring loaded plunger shaped and positioned to cause said first and second locking bars to move laterally such that said projections come into engagement with said groove.

16. A user replaceable electrode cartridge structured and dimensioned to be installed into a housing beneath a removable lid of the housing by a user of a spa and comprising:
a handle shaped to be grippable by the spa user to insert the electrode cartridge into the housing and to pull the electrode cartridge out of the housing for replacement;
first and second electrodes mounted beneath the handle for generating chlorine from spa water; and
first and second electrical contacts, each positioned opposite one another on an exterior side surface of said electrode cartridge, one of the first and second electrical contacts being electrically connected to a respective one of said first and second electrodes; the electrode cartridge further comprising:
first and second locking bars having first and second projections on respective outer ends thereof and mounted to slide laterally in said cartridge such that said first and second projections can come into engagement with a groove on the housing to lock said cartridge in position; and
a spring loaded plunger shaped and positioned to cause said first and second locking bars to move laterally such that said projections come into engagement with said groove.

17. An electrode cartridge configured to generate chlorine and shaped to be installable by a user of a spa into a housing mounted in the spa and comprising:
a handle shaped to be grippable by the user of the spa to insert the electrode cartridge into the housing and to pull the electrode cartridge out of the housing for replacement;
first and second electrodes mounted beneath the handle so as to extend into said housing and being constructed to generate chlorine to purify spa water, the first and second electrodes being spaced apart horizontally so as to create a flow path for electrical a current through the spa water from one of the first and second electrodes to the other of the first and second electrodes; and
first and second electrical contacts positioned on opposite sides of the electrode cartridge so as to respectively contact first and second electrical contacts on the housing when the electrode cartridge is in an installed position in the housing, the first electrical contact being electrically connected to one of said first and second electrodes, the second electrical contact being electrically connected to the other one of the first and second electrodes, one of the first and second electrical contacts comprising an entry point for electrical current into said electrode cartridge, the other of the first and second electrical contacts comprising an exit point for electrical current out of said electrode cartridge.

18. The electrode cartridge of claim 17 wherein the first and second electrodes each include a vertical portion which forms into a horizontal base portion from which extends an outwardly curved spring arm electrical contact, the outwardly extending spring arm electrical contact comprising one of said first and second electrical contacts positioned on opposite sides of the electrode cartridge.

19. The electrode cartridge of claim 17 further comprising an electrode holder shaped to be insertable into said housing and configured to mount the first and second electrodes so as to extend downwardly from a bottom surface of said electrode holder and so as to be spaced apart horizontally from one another.

20. The electrode cartridge of claim 19 wherein the electrode holder further comprises first and second horizontally lying receptacles shaped such that the horizontal base portion of each of the first and second electrodes respectively fit therein.

21. The electrode cartridge of claim 20 wherein each horizontal base portion is held in place in its respective mating receptacle by a bottom surface of the handle of the electrode cartridge.

22. The electrode cartridge of claim 17 wherein the first and second electrical contacts of the electrode cartridge are positioned so that upon initial installation of the electrode cartridge, the first and second electrical contacts of the cartridge are initially located above and spaced vertically apart from the first and second contacts of the housing into which the electrode cartridge is shaped to be installed and so that they thereafter come into electrical contact with a respective one of the first and second contacts of the housing as the electrode cartridge is inserted further into the housing.

23. The electrode cartridge of claim 22 wherein the first and second electrical contacts of the electrode cartridge are further so positioned as to enable the flow path of electrical current into and out of the electrode cartridge to be broken by the single step of pulling the electrode cartridge out of the housing.

24. The electrode cartridge of claim 17 wherein the electrode cartridge is designed and constructed to be removed as a unit from the housing and thrown away.

25. The electrode cartridge of claim 17 wherein the electrode cartridge is configured such that the first and second electrical contacts of the electrode cartridge constitute the only respective entry and exit points for electrical current into and out of the electrode cartridge.

26. The electrode cartridge of claim 17 wherein the electrode cartridge comprises a free standing unit and wherein, as a free standing unit, said first and second electrical contacts of the electrode cartridge constitute the only respective entry and exit points for electrical current into and out of the cartridge.

27. An electrode cartridge configured to generate chlorine and shaped to be installed by a user of a spa into a housing mounted in the spa and comprising:
   a handle shaped to be grippable by the user of the spa to insert the electrode cartridge into the housing and to pull the electrode cartridge out of the housing for replacement;
   an electrode holder insertable into said housing and having a circular side surface, the electrode holder positioning first and second electrodes to extend beneath said holder and into said housing, the first and second electrodes being constructed to generate chlorine to purify spa water;
   sealing means located on said circular side surface so as to define (a) a wet spa water containing portion of the housing and (b) a dry portion of the housing when the electrode cartridge is in an installed position in the housing, the dry portion of the housing being located above the wet spa water containing portion of the housing;
   the electrode holder being further configured to position the first and second electrodes in spaced apart relation in the wet portion of the housing so as to create a flow path for electrical current between the first and second electrodes; and
   first and second electrical contacts, each located on a side surface of said electrode cartridge and positioned to respectively contact one of first and second electrical contacts, each located on a side surface of the dry portion of the housing when the electrode cartridge is in the installed position in the housing.

28. The electrode cartridge of claim 27 wherein said sealing means comprises an O-ring.

29. The electrode cartridge of claim 27 wherein said sealing means is installed in a groove in said circular periphery.

30. The electrode cartridge of claim 29 wherein said sealing means comprises an O-ring.

31. The electrode cartridge of claim 27 further comprising a first electrical conductor path electrically connecting said first electrode with the first electrical contact of the electrode cartridge and a second electrical conductor path electrically connecting said second electrode with the second electrical contact of the electrode cartridge.

32. The electrode cartridge of claim 27 wherein the first and second electrodes each include a vertical portion which forms into a horizontal base portion from which extends an outwardly curved spring arm electrical contact, each of the outwardly extending spring arm electrical contacts comprising one of said first and second electrical contacts each located on a side surface of said electrode cartridge.

33. The electrode cartridge of claim 32 wherein the electrode holder is cylindrical in shape and further comprises first and second horizontally lying receptacles shaped such that the horizontal base portions of each of the first and second electrodes respectively fit therein.

34. The electrode cartridge of claim 33 wherein a bottom surface of the handle of the electrode cartridge is configured to hold each horizontal base portion in place in its respective mating receptacle.

35. The electrode cartridge of claim 27 wherein the first and second electrical contacts of the electrode cartridge are further positioned such that upon initial installation of the electrode cartridge, the electrical contacts of the cartridge are initially positioned above and spaced vertically apart from the respective first and second electrical contacts located in the dry portion of the housing.

36. The electrode cartridge of claim 35 wherein each of the first and second electrical contacts of the electrode cartridge comprise an upwardly extending electrical contact arm which is spring biased outwardly away from a side surface of the electrode cartridge and compressible inwardly toward said side surface against the spring bias.

37. The electrode cartridge of claim 27 wherein the electrode cartridge is designed and constructed to be removed as a unit from the housing and thrown away.

38. The electrode cartridge of claim 27 wherein the electrode cartridge is configured such that the first and second electrical contacts of the electrode cartridge constitute the only respective entry and exit points for electrical current into and out of the electrode cartridge.

39. The electrode cartridge of claim 27 so configured that the flow path of electrical current through the housing is broken by the single step of pulling the electrode cartridge out of the housing.

40. The electrode cartridge of claim 27 wherein the electrode cartridge comprises a free standing unit and wherein, as a free standing unit, said first and second electrical contacts of the electrode cartridge constitute the only respective entry and exit points for electrical current into and out of the cartridge.

41. An electrode cartridge constructed to generate chlorine and to purify spa water and further shaped to be installed downwardly into a housing by a user of a spa, the housing having first and second side-mounted electrical contacts each positioned opposite one another on an inner side surface of the housing, the electrode cartridge comprising:
   a handle grippable by the user to insert the electrode cartridge into the housing and to pull the electrode cartridge out of the housing for replacement;
   an electrode holder located beneath the handle;
   first and second electrodes mounted in said electrode holder and positioned to extend downwardly from a bottom surface of the electrode holder so as to extend into said housing when the electrode cartridge is in an installed position in the housing, the first and second electrodes being constructed to generate chlorine to purify spa water, the first and second electrodes being spaced horizontally apart so as to create a flow path for electrical current between them; and
   first and second electrical contacts, each positioned opposite one another on opposite side surfaces of said electrode cartridge and further positioned so as to be initially located above and out of electrical contact with the first and second side mounted electrical contacts of the housing as installation of the cartridge into the housing begins, and so as to thereafter come into electrical contact with a respective one of the first and second side-mounted electrical contacts of the housing as the electrode cartridge is inserted further downwardly into the housing and comes into an installed position in the housing.

42. The electrode cartridge of claim 41 wherein each of the first and second electrical contacts of the electrode cartridge comprise an upwardly extending electrical contact arm which is spring biased outwardly away from a side surface of the electrode cartridge and compressible inwardly toward said side surface against the spring bias.

43. The electrode cartridge of claim 41 wherein the electrode cartridge is designed and constructed to be removed as a unit from the housing and thrown away.

44. The electrode cartridge of claim 41 wherein the electrode cartridge is configured such that the first and second electrical contacts of the electrode cartridge constitute the only respective entry and exit points for electrical current into and out of the electrode cartridge.

45. The electrode cartridge of claim 41 wherein the first and second electrical contacts are further so positioned as to enable the flow path of electrical current into and out of the electrode cartridge to be broken by the single step of pulling the electrode cartridge out of the housing.

46. The electrode cartridge of claim 45 wherein the electrode cartridge is further configured such that the first and second electrical contacts of the electrode cartridge constitute the only respective entry and exit points for electrical current into and out of the electrode cartridge.

47. An electrode cartridge constructed to generate chlorine and shaped to be installed downwardly into a housing by a user of a spa, the housing having first and second electrical contacts each positioned on an inner side surface of the housing, the electrode cartridge comprising:
  a handle grippable by the user to insert the electrode cartridge into the housing and to pull the electrode cartridge out of the housing for replacement;
  an electrode holder located beneath the handle;
  first and second electrodes mounted in said electrode holder and positioned to extend downwardly from a bottom surface of the electrode holder so as to extend into said housing when the electrode cartridge is in an installed position in the housing, the first and second electrodes being constructed to generate chlorine to purify spa water, the first and second electrodes being spaced horizontally apart so as to create a flow path for electrical current between them;
  first and second outwardly curved spring arm electrical contacts, each positioned on a side surface of said electrode cartridge and further positioned so as to be initially located above and out of electrical contact with the first and second electrical contacts of the housing and so as to thereafter come into electrical contact with a respective one of the first and second electrical contacts of the housing as the electrode cartridge is inserted downwardly into the housing and comes into an installed position in the housing; and
  wherein the first and second electrodes each include a vertical portion which forms into a horizontal base portion from which extends a respective one of said first and second outwardly curved spring arm electrical contacts, each horizontal base portion being positioned in a respective horizontally disposed receptacle located in said electrode holder and being held in place in its respective receptacle by a bottom surface of said handle.

48. An electrode cartridge comprising:
  a single piece first electrode including a vertical portion constructed to generate chlorine, the vertical portion forming seamlessly into a horizontally extending base portion which then forms seamlessly into an upwardly extending electrical contact arm which is spring biased outwardly away from a side surface of the electrode cartridge and compressible inwardly toward said side surface against the spring bias; and
  a single piece second electrode including a vertical portion constructed to generate chlorine, the vertical portion forming seamlessly into a horizontally extending base portion which then forms seamlessly into an upwardly extending electrical contact arm which is spring biased outwardly away from a side surface of the electrode cartridge and compressible inwardly toward said side surface against the spring bias.

49. An electrode cartridge constructed to generate chlorine and shaped to be installed by a user of a spa into a housing mounted in the spa, the housing having first and second side-mounted electrical contacts, each mounted on a side surface of said housing, the electrode cartridge comprising:
  an electrode holder insertable into said housing and having a circular side surface, the electrode holder positioning first and second electrodes to extend beneath said holder and into said housing, the first and second electrodes being constructed to generate chlorine from spa water;
  a handle attached to said electrode holder and shaped to be grippable by the user of the spa to enable the user to insert the electrode cartridge into the housing and to pull the electrode cartridge out of the housing for replacement;
  sealing means located on said circular side surface so as to define (a) a wet spa water containing portion of the housing and (b) a dry portion of the housing, the dry portion of the housing being located above the wet spa water containing portion of the housing and further being located such that said first and second side-mounted electrical contacts reside therein when the electrode cartridge is in an installed position in the housing;
  the electrode holder being further configured to position the first and second electrodes in spaced apart relation in the wet portion of the housing so as to create a flow path for electrical current between the first and second electrodes; and
  first and second electrical contacts, each positioned on a side surface of said electrode cartridge (a) so as to be initially located above and out of electrical contact with the first and second side-mounted electrical contacts at the beginning of installation of the electrode cartridge into the housing, and (b) so as to thereafter come into electrical contact with a respective one of the first and second side-mounted electrical contacts as the electrode cartridge is inserted downwardly into the housing and comes into an installed position in the housing.

50. The electrode cartridge of claim 49 wherein said sealing means comprises an O-ring.

51. The electrode cartridge of claim 49 wherein said sealing means is installed in a groove in said circular periphery.

52. The electrode cartridge of claim 51 wherein said sealing means comprises an O-ring.

53. The electrode cartridge of claim 49 wherein each of the first and second electrical contacts of the electrode cartridge comprise an upwardly extending electrical contact arm which is spring biased outwardly away from a side surface of the electrode cartridge and compressible inwardly toward said side surface against the spring bias.

54. The electrode cartridge of claim 49 wherein the first and second electrical contacts are further so positioned as to enable the flow path of electrical current into and out of the electrode cartridge to be broken by the single step of pulling the electrode cartridge out of the housing.

55. An electrode cartridge shaped to be installed downwardly into a housing by a user of a spa, the housing having first and second side-mounted electrical contacts each positioned on an inner side surface of the housing, the electrode cartridge comprising:

an electrode holder;

first and second electrodes mounted in said electrode holder and positioned to extend downwardly from a bottom surface of the electrode holder so as to extend into said housing when the electrode cartridge is in an installed position in the housing, the first and second electrodes being spaced horizontally apart so as to create a flow path for electrical current between them; and first and second electrical contacts, each positioned on a side surface of said electrode cartridge and further positioned (a) so as to be initially located above and out of electrical contact with the first and second side mounted electrical contacts of the housing at the beginning of installation of the electrode cartridge into the housing, and (b) so as to thereafter come into electrical contact with a respective one of the first and second side mounted electrical contacts of the housing as the electrode cartridge is inserted downwardly into the housing and comes into an installed position in the housing.

56. The electrode cartridge of claim 55 wherein the first and second electrical contacts are further so positioned as to enable the flow path of electrical current into and out of the electrode cartridge to be broken by the single step of pulling the electrode cartridge out of the housing.

\* \* \* \* \*